US00PP34095P2

(12) United States Plant Patent
van Sambeek

(10) Patent No.: US PP34,095 P2
(45) Date of Patent: Apr. 5, 2022

(54) *IBERIS* PLANT NAMED 'DOIBEWHISHA'

(50) Latin Name: *Iberis sempervirens*
Varietal Denomination: Doibewhisha

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/499,130

(22) Filed: Oct. 12, 2021

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 5/02
See application file for complete search history.

(56) References Cited

PUBLICATIONS

PLUTO UPOVROM Citation for 'Doibewhisha' as per QZ PBR 20211659; Aug. 15, 2021; 1 page.*

* cited by examiner

*Primary Examiner* — Kent L Bell
(74) *Attorney, Agent, or Firm* — C. Anne Whealy

(57) ABSTRACT

A new and distinct cultivar of *Iberis* plant named 'Doibewhisha', characterized by its compact, upright to outwardly spreading and uniformly mounding plant habit; vigorous growth habit; freely branching habit; dense and bushy habit; relatively late flowering; numerous dense inflorescences with white-colored flowers; and good container and garden performance.

1 Drawing Sheet

Botanical designation: *Iberis sempervirens*.
Cultivar denomination: 'DOIBEWHISHA'.

STATEMENT REGARDING PRIOR DISCLOSURES BY INVENTOR & APPLICANT/ASSIGNEE

An European Community Plant Breeder's Rights application for the instant plant was filed by the Inventor/Applicant on Jun. 21, 2021, application number 2021/1659. Foreign priority is not claimed to this application.

The Inventor/Applicant assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Iberis* plant, botanically known as *Iberis sempervirens* and hereinafter referred to by the name 'Doibewhisha'.

The new *Iberis* plant is a product of a planned breeding program conducted by the Inventor in Aalsmeer, The Netherlands. The objective of the breeding program is to create new freely branching *Iberis* plants with large flowers and large inflorescences.

The new *Iberis* plant originated from an open-pollination in April, 2017 in Aalsmeer, The Netherlands of a proprietary selection of *Iberis sempervirens* identified as code number IB16-000155-002, not patented, as the female, or seed parent with an unknown selection of *Iberis sempervirens* as the male, or pollen, parent. The new *Iberis* plant was discovered and selected by the Inventor as a single flowering plant from within the progeny of the stated open-pollination in a controlled greenhouse environment in Aalsmeer, The Netherlands in April, 2018.

Asexual reproduction of the new *Iberis* plant by vegetative terminal cuttings in a controlled greenhouse environment in since June, 2018 has shown that the unique features of this new *Iberis* plant are stable and reproduced true to type in successive generations.

SUMMARY OF THE INVENTION

Plants of the new *Iberis* have not been observed under all possible combination of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doibewhisha'. These characteristics in combination distinguish 'Doibewhisha' as a new and distinct *Iberis* plant:

1. Compact, upright to outwardly spreading and uniformly mounding plant habit.
2. Vigorous growth habit.
3. Freely branching habit; dense and bushy habit.
4. Relatively late flowering.
5. Numerous dense inflorescences with white-colored flowers.
6. Good container and garden performance.

Plants of the new *Iberis* differ primarily from plants of the female parent selection in flower size as plants of the new *Iberis* have larger flowers than plants of the female parent selection.

Plants of the new *Iberis* can be compared to plants of *Iberis sempervirens* 'Snow Cone', not patented. In side-by-side comparisons, plants of the new *Iberis* differ from plants of 'Snow Cone' in the following characteristics:

1. Plants of the new *Iberis* flower later than plants of 'Snow Cone'.
2. Plants of the new *Iberis* have larger flowers than plants of 'Snow Cone'.

BRIEF DESCRIPTION OF THE PHOTOGRAPH

The accompanying photograph illustrates the overall appearance of the new *Iberis* plant showing the colors as true as it is reasonably possible to obtain in colored reproductions of this type. Colors in the photograph may differ slightly from the color values cited in the detailed botanical description which accurately describe the colors of the new *Iberis* plant.

The photograph is a side perspective view of a typical flowering plant of 'Doibewhisha' grown in a container.

DETAILED BOTANICAL DESCRIPTION

The aforementioned photograph and following observations and measurements describe plants grown during the spring in 17-cm containers in an outdoor nursery in Aalsmeer, The Netherlands and under cultural practices typical of commercial *Iberis* production. During the production of the plants, average daily temperatures were 21° C. and average night temperatures were 15° C. Plants were pinched two weeks after planting and were 44 weeks old when the photograph and description were taken. In the following description, color references are made to The Royal Horticultural Society Colour Chart, Second Edition, except where general terms of ordinary dictionary significance are used.

Botanical classification: *Iberis sempervirens* 'Doibewhisha'.

Parentage:

*Female, or seed, parent*.—Proprietary selection of *Iberis sempervirens* identified as code number IB16-000155-002, not patented.

*Male, or pollen, parent*.—Unknown selection of *Iberis sempervirens*, not patented.

Propagation:

*Type*.—Terminal vegetative cuttings.

*Time to initiate roots, summer*.—About 16 days at temperatures about 26° C.

*Time to initiate roots, winter*.—About three weeks at temperatures about 23° C.

*Time to produce a rooted cutting, summer*.—About 24 days at temperatures about 23° C.

*Time to produce a rooted cutting, winter*.—About four weeks at temperatures about 5° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching habit; medium density.

Plant description:

*Plant and growth habit*.—Perennial, good performance as a container and garden plant; compact, upright to somewhat outwardly spreading and uniformly mounding plant habit; vigorous growth habit; freely branching habit; about ten primary branches develop per plant each with about 28 secondary laterals; dense and bushy habit.

*Plant height*.—About 15 cm.

*Plant diameter*.—About 32 cm.

Lateral branch description:

*Length*.—About 13 cm.

*Diameter*.—About 4 mm.

*Internode length*.—About 2 mm.

*Strength*.—Strong.

*Aspect*.—Upright to about 50° from vertical.

*Texture and luster*.—Smooth, glabrous; glossy.

*Color, developing*.—Close to 144B.

*Color, developed*.—Close to 143C.

Leaf description:

*Arrangement*.—Alternate, simple; sessile.

*Length*.—About 1.7 cm.

*Width*.—About 4 mm.

*Shape*.—Lanceolate.

*Apex*.—Acute.

*Base*.—Cuneate.

*Margin*.—Entire.

*Texture and luster, upper and lower surfaces*.—Smooth, glabrous; glossy.

*Venation pattern*.—Single midvein discernible.

*Color*.—Developing leaves, upper and lower surfaces: Close to 143B. Fully expanded leaves, upper surface: Close to 137A; venation, close to 137A. Fully expanded leaves, lower surface: Close to 143A; venation, close to 143C.

Flower description:

*Flower arrangement and habit*.—Large, asymmetrical cruciferous flowers arranged in terminal corymbs; flowers face mostly upright; freely flowering habit with about 22 flowers per inflorescence with about 5100 flowers developing during the flowering season.

*Fragrance*.—Faintly fragrant; pleasant.

*Natural flowering season*.—Plants flower during the spring in The Netherlands; flowers not persistent.

*Inflorescence height*.—About 1.5 cm.

*Inflorescence diameter*.—About 3.5 cm.

*Flower diameter*.—About 5 mm by 13 mm.

*Flower depth*.—About 9 mm.

*Flower depth*.—About 1.3 cm.

*Flower buds*.—Length: About 3 mm. Diameter: About 4 mm. Shape: Ovoid. Texture and luster: Smooth, glabrous; matte. Color: Close to 155D.

*Petals*.—Arrangement: Four petals; two smaller upper petals and two larger lower petals. Length: Upper petals: About 4 mm. Lower petals: About 9 mm. Width: Upper petals: About 4 mm. Lower petals: About 6 mm. Shape: Obovate. Apex: Obtuse. Base: Obtuse. Margin: Entire; not undulate. Texture and luster, upper and lower surfaces: Smooth, glabrous; matte. Color: When opening, upper and lower surfaces: Close to 155D. Fully opened, upper and lower surfaces: Close to 155D; color does not change with subsequent development.

*Sepals*.—Arrangement: Calyx cup-shaped with four sepals in a single whorl. Calyx length: About 2 mm. Calyx diameter: About 4 mm. Length: About 2 mm. Width: About 2 mm. Shape: Obovate. Apex:

Rounded. Base: Obtuse. Margin: Entire. Texture and luster, upper and lower surfaces: Smooth, glabrous; semi-glossy. Color, upper surface: Close to 146A; one sepal tinged with close to 77B. Color, lower surface: Close to 146A.

*Peduncles*.—Length: About 1.5 cm. Diameter: About 3 mm. Angle: About 30° from lateral branch axis. Strength: Moderately strong. Texture and luster: Smooth, glabrous; glossy. Color: Close to 144A.

*Pedicels*.—Length: About 7 mm. Diameter: About 1 mm. Angle: Erect to 45° from peduncle axis depending on position on corymb. Strength: Flexible. Texture and luster: Smooth, glabrous; glossy. Color: Close to 145A.

*Reproductive organs*.—Stamens: Quantity: Six per flower. Filament length: About 3 mm. Filament color: Close to 154C. Anther shape: Elliptic. Anther length: About 1 mm. Anther color: Close to 9A. Pollen amount: Moderate. Pollen color: Close to 6D. Pistils: Quantity: One per flower. Pistil length: About 4 mm. Style length: About 2 mm. Style color: Close to 145B. Stigma diameter: About 0.5 mm. Stigma shape: Rounded, capitate. Stigma color: Close to 144A. Ovary color: Close to 145B.

*Seeds and fruits*.—To date, seed and fruit development have not been observed on plants of the new *Iberis*.

Pathogen & pest resistance: To date, plants of the new *Iberis* have not been observed to be resistant to pathogens and pests common to *Iberis* plants.

Garden performance: Plants of the new *Iberis* have been observed to have good garden performance and to tolerate wind, rain, temperatures ranging from −35° C. to 35° C. and to be suitable for USDA Hardiness Zones 3 through 9.

It is claimed:

1. A new and distinct *Iberis* plant named 'Doibewhisha' as illustrated and described.

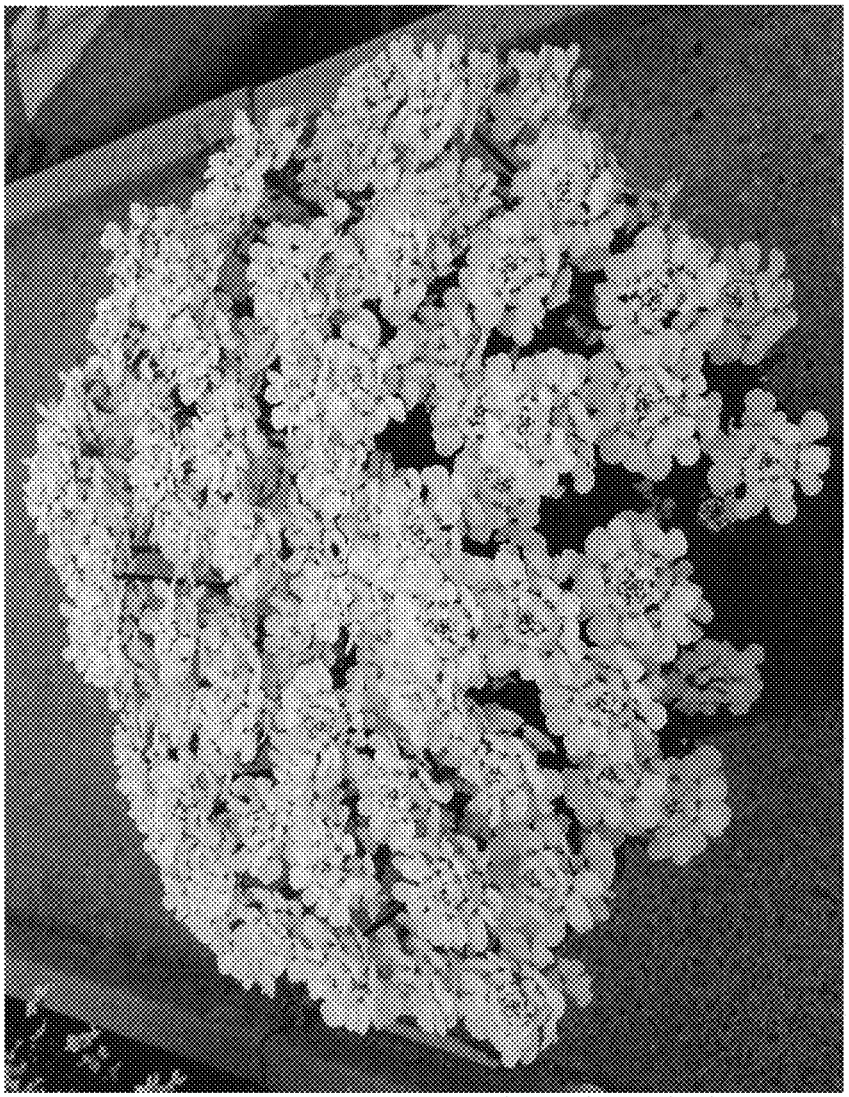

* * * * *